United States Patent [19]

Sato et al.

[11] 4,409,323

[45] Oct. 11, 1983

[54] SILVER HALIDE PHOTOGRAPHIC MATERIAL

[75] Inventors: Ryosuke Sato, Hino; Yuji Hotta; Katsumi Matsuura, both of Hachioji, all of Japan

[73] Assignee: Konishiroku Photo Industry Co., Ltd., Tokyo, Japan

[21] Appl. No.: 234,442

[22] Filed: Feb. 13, 1981

[30] Foreign Application Priority Data

Feb. 15, 1980 [JP] Japan ................................. 55-17644

[51] Int. Cl.$^3$ .............................................. G03C 1/40
[52] U.S. Cl. .................................... 430/544; 430/543; 430/549; 430/550; 430/553; 430/555; 430/557; 430/558; 430/559; 430/957; 430/958
[58] Field of Search ............... 430/544, 549, 550, 551, 430/553, 555, 557, 558, 559, 957, 958, 543

[56] References Cited

U.S. PATENT DOCUMENTS

| | | |
|---|---|---|
| 2,298,443 | 10/1942 | Weissberger . |
| 2,311,082 | 2/1943 | Porter et al. . |
| 2,343,703 | 3/1944 | Porter et al. . |
| 2,367,531 | 1/1945 | Salminen et al. . |
| 2,369,489 | 2/1945 | Porter et al. . |
| 2,407,210 | 9/1946 | Weissberger et al. . |
| 2,423,730 | 7/1947 | Salminen et al. . |
| 2,474,293 | 6/1949 | Weissberger et al. . |
| 2,600,788 | 6/1952 | Loria et al. . |
| 2,772,162 | 11/1956 | Salminen et al. . |
| 2,875,057 | 2/1959 | McCrossen et al. . |
| 2,895,826 | 7/1959 | Salminen et al. . |
| 2,908,573 | 10/1959 | Bush et al. . |
| 3,002,836 | 10/1961 | Vittum et al. . |
| 3,034,892 | 5/1962 | Gledhill et al. . |
| 3,041,236 | 6/1962 | Stecker . |
| 3,048,194 | 8/1962 | Huthsing, Sr. et al. . |
| 3,062,653 | 11/1962 | Weissberger et al. . |
| 3,148,062 | 9/1964 | Whitmore et al. . |
| 3,152,896 | 10/1964 | Tuite . |
| 3,227,554 | 1/1966 | Barr et al. . |
| 3,265,506 | 8/1966 | Weissberger et al. . |
| 3,277,554 | 10/1966 | Morse . |
| 3,384,657 | 5/1968 | Weissberger et al. . |
| 3,447,928 | 6/1969 | Loria .................................. 430/557 |
| 3,519,429 | 7/1970 | Lestina . |
| 3,615,506 | 10/1971 | Abbott et al. . |
| 3,617,291 | 11/1971 | Sawdey . |
| 3,632,345 | 1/1972 | Marx et al. . |
| 3,705,801 | 12/1972 | Holtz . |
| 3,733,201 | 5/1973 | Barr . |
| 3,926,631 | 12/1975 | Arai et al. .......................... 430/372 |
| 3,928,041 | 12/1975 | Fujiwhara et al. . |
| 3,958,993 | 5/1976 | Fujiwhara et al. . |
| 3,961,959 | 6/1976 | Fujiwhara et al. . |
| 4,009,038 | 2/1977 | Arai et al. .......................... 430/551 |
| 4,010,035 | 3/1977 | Fujiwhara et al. ................. 430/557 |
| 4,012,258 | 3/1977 | Kojima et al. ..................... 430/557 |
| 4,026,709 | 5/1977 | Piller et al. ......................... 430/557 |
| 4,040,835 | 8/1977 | Arai et al. .......................... 430/555 |
| 4,248,962 | 2/1981 | Lau ..................................... 430/544 |
| 4,283,486 | 8/1981 | Aono et al. ........................ 430/557 |

FOREIGN PATENT DOCUMENTS 2010818A 7/1979 United Kingdom .

Primary Examiner—J. Travis Brown
Attorney, Agent, or Firm—Finnegan, Henderson, Farabow, Garrett & Dunner

[57] ABSTRACT

A silver halide photographic material containing a coupler capable of releasing a photographically useful group in a controllable timing.

9 Claims, No Drawings

SILVER HALIDE PHOTOGRAPHIC MATERIAL

The present invention relates to a silver halide photographic material containing a new compound of photographic application capable of releasing a photographically useful group in a controllable timing.

Various means are known to make use of a compound of photographic application in releasing a photographically useful group in correspondence with the image pattern. For example, U.S. Pat. Nos. 3,148,062, 3,277,554 and 3,705,801 disclose methods to release a development inhibitor, a photographic dye or a bleach inhibitor from the coupling site of the photographic coupler as a result of the reaction of such photographic coupler with the oxidized color developing agent. These compounds are induced to release a photographically useful group without adjustments to control the releasing timing.

Advancedly UK patent application GB No. 2010818A discloses a coupler which releases the photographically useful group on the color development with capability of control timing of the releasing. According to the description, the reaction of the coupler with the oxidized color developing agent leads to the first stage of cleavage, followed by an intramolecular nucleophilic displacement reaction, which causes the second stage of cleavage for the release of the photographically useful group, so, parameters may be controlled allowing adjustments over a wide range including those required for the timing of the effect exerted by the photographically useful group, the moving distance thereof, etc.

However, when the compound is used, the hydroxyl ion in the color developer also shares the nucleophilic displacement reaction, which results in a defect that the photographically useful group is released not only in exposed areas but in unexposed areas inspite of the expectation of the effect only in exposed areas, and that the controllable timing is limited to relatively shorter range.

The object of the present invention is to provide a compound free from the disadvantage mentioned above, and a photographic material containing the compound therein. More definitely the object is to provide a compound and a photographic material containing the compound, which is hard to decompose by hydroxyl ion and improved in a property of imagewise releasing a photographically useful group, on a coupling reaction, permitting control of time of release, rate of release, rate of diffusion, etc.

According to the present invention, the compound comprises a coupling group, a photographically useful group a timing group joining the coupler and photographically useful groups, which is cleavable from said coupler group on reaction with an oxidized color developing agent and the resulting cleaved timing and photographically useful group is able to undergo electron transfer along a conjugated system in the timing group whereby the photographically useful group is cleaved.

In the present invention, compounds that are preferable for use are represented by the formula as follows:

A-TIME-PUG    (1)

where "A" is the coupler group capable of coupling reaction with the oxidized color developing agent, "TIME" the timing group and "PUG" the photographically useful group.

Any compound may be used for the coupler group A as far as it can react with the oxidized color developing agent to release the group -TIME-PUG. Examples of the coupler group include one which will form a colored product or a colorless product on coupling reaction with the oxidized color developing agent. The coupler group A may have no ballasting group or may be ballasted with an oil soluble or aliphatic group or groups. The group -TIME-PUG is attached to the component A at the coupling site, which is capable of coupling reaction with the oxidized color developing agent. The timing group joining the PUG and the component A may be an arbitrary organic group characterized by such a property that it can be cleaved from the PUG as a result of an electron transfer along a conjugated system toward PUG after the group -TIME-PUG is cleaved from the component A.

In the present invention, the term "conjugated system" refers to a form of bonding generally known as such in the field of chemistry, namely, the one in which a single bond and a double or triple bond appear alternatively in the chemical formula. Accordingly, it is assumed that the lone pair electron on the fragment -TIME-PUG cleaved from the component A is transferred along a conjugated system to ultimately break the bond between the TIME and PUG.

Examples of the timing group are formulated in the following formula:

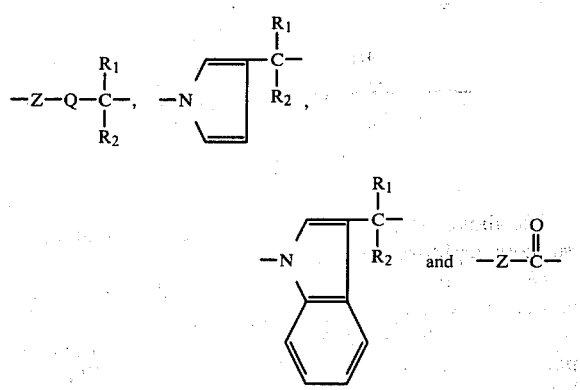

wherein the left hand side is attached to the coupler group, Z is O, S or

$R_1$, $R_2$ and $R_3$ are individually a hydrogen atom, alkyl or aryl group, Q ia 1,2- or 1,4-phenylene or naphthylene group. The phenylene or naphthylene may have a such substituent as halogen atom, alkyl, alkoxy, —CN, —$NO_2$, —NHCOR or —COOR wherein R is alkyl.

In case the TIME group forms quinonemethide or naphthoquinonemethide on the final cleavage, the compound of the present invention includes one represented by the following general formula:

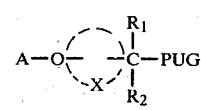   (2)

where "A" and "PUG" are the same as defined in the general formula (1) while "X" represents atoms necessary to complete a substituted or nonsubstituted benzene or naphthalene nucleus and "R₁" and "R₂" individually represent a hydrogen atom, alkyl group or aryl group, with the group

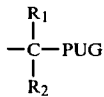

being joined at the para or ortho position relative to the oxygen atom.

The compound as represented by the above general formula (2) is cleaved as it reacts with the oxidized color developing agent, first forming a compound as represented by the following general formula (3), which is then recleaved through an electron transfer along the conjugated system to form a compound as represented by the following general formula (4) while releasing the PUG:

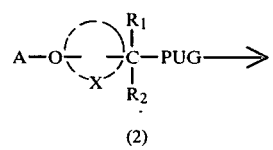

(2)

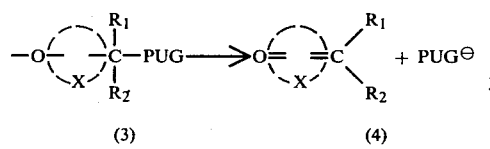

(3)    (4)

The above compound (4) is called either quinonemethide or naphthoquinonemethide.

Next, as an example of the compound of the present invention, a compound comprising a timing group which will ultimately form a quinonemethide compound and phenylmercaptotetrazole as the PUG is selected to illustrate the process of the present invention diagrammatically:

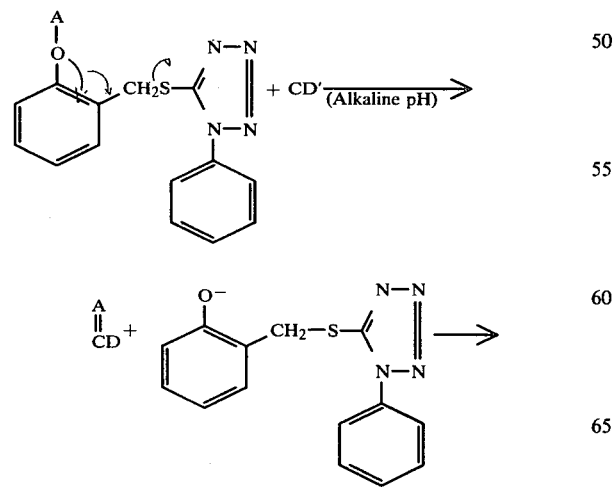

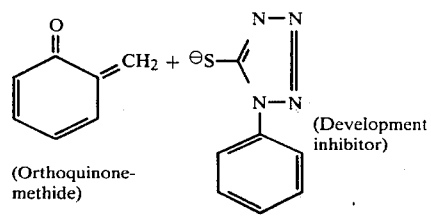

(Orthoquinonemethide)    (Development inhibitor)

where "CD" represents the oxidized color developing agent.

In the above diagram, upon the coupling reaction the compound of the present invention cleaves to release the timing group bonding to the photographically useful group (development inhibitor in this case), which is then recleaved by an electron transfer along the conjugated system as indicated by arrows to form orthoquinonemethide while releasing the development inhibitor.

Further, referring to a compound that uses a timing group other than the one used above as another example of the compound of the present invention, the process is again illustrated diagrammatically:

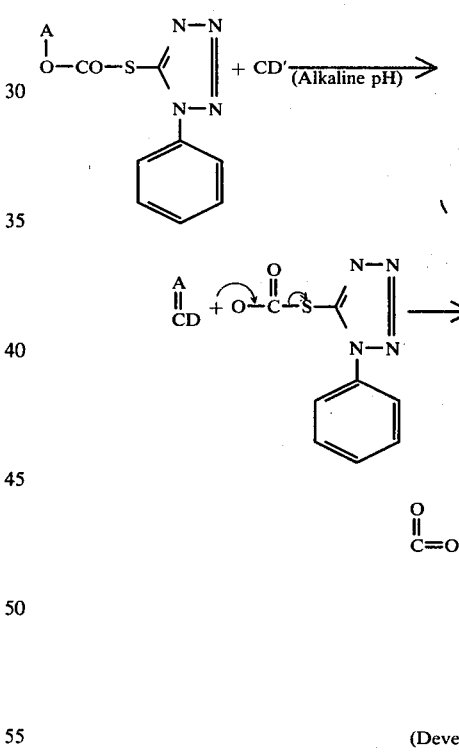

(Development inhibitor)

where "A" and "CD" are the same as defined previously. Also in this case, in the fragment that is released from the compound after its reaction with CD' a lone pair electron located on the oxygen atom is conjugated with the carbonyl π electrons.

As for the coupling group capable of undergoing a coupling reaction with the oxidized color developing agent, residues of couplers generally employed in the color photographic material are cited.

For example, for the yellow coupler, benzoylacetanilide derivatives or pivaloylacetanilide derivatives as disclosed in U.S. Pat. Nos. 2,298,443, 2,407,210, 2,875,057, 3,048,194, 3,265,506, and 3,447,928, "Farbkuppler-eine Literaturubersicht", Agfa Mitteilung (Band II), pp. 112–126 (1961), etc. may be used. Further, for the magenta coupler, various compounds including pyrazolone derivatives as disclosed in U.S. Pat. Nos. 2,369,489, 2,343,703, 2,311,082, 2,600,788, 2,908,573, 3,062,653, 3,152,896 and 3,519,429, the aforementioned Agfa Mitteilung (Band II), pp. 126–156 (1961), etc. may be used. Further, for the cyan coupler, naphthol and phenol derivatives as disclosed in U.S. Pat. Nos. 2,367,531, 2,423,730, 2,474,293, 2,772,162, 2,895,826, 3,002,836, 3,034,892 and 3,041,236, the aforementioned Agfa Mitteilung (Band II), pp. 156–175 (1961), etc. may be used.

Beside these couplers, black dye forming couplers as disclosed in West Germany Pat. OLS No. 2,644,194 may be used.

In the meantime, the coupler group which can undergo coupling reaction with the oxidized color developing agent resulting formation of no coloring dye, as represented by cyclic carbonyl compounds, may also be employed for the compound of the present invention. For these compounds, a description is given in U.S. Pat. Nos. 3,632,345, 3,928,041, 3,958,993 and 3,961,959, British Pat. No. 861,138, etc.

For the photographically useful group, any component may be used as far as it is useful when made available in correspondence with the image pattern within the photographic element as it is released.

As concrete examples of the photographically useful group, the development inhibitor or accelerator, bleach inhibitor or accelerator, developing agent, fixing agent, silver halide solvent, silver-complex forming agent, hardening agent, tanning agent, toning agent, fogging agent, antifoggant, chemical or optical sensitizer and desensitizer, photographic dye and its precursor, or couplers such as the competitive coupler, coloring coupler or DIR coupler, may be cited.

Among the above photographically useful groups, the most preferable is the development inhibitor, which is well known to the person skilled in the photographic industry. Typical examples of the development inhibitor are compounds of mercaptotetrazole, selenotetrazole, mercaptobenzothiazole, selenobenzothiazole, mercaptobenzoxazole, selenobenzoxazole, mercaptobenzimidazole, selenobenzimidazole, benzodiazole, benzotriazole and iodides as disclosed in U.S. Pat. Nos. 3,227,554, 3,384,657, 3,615,506, 3,617,291 and 3,733,201, and British Pat. No. 1,450,479.

Specific examples of the compound of the present invention are given below. Illustrative compounds:

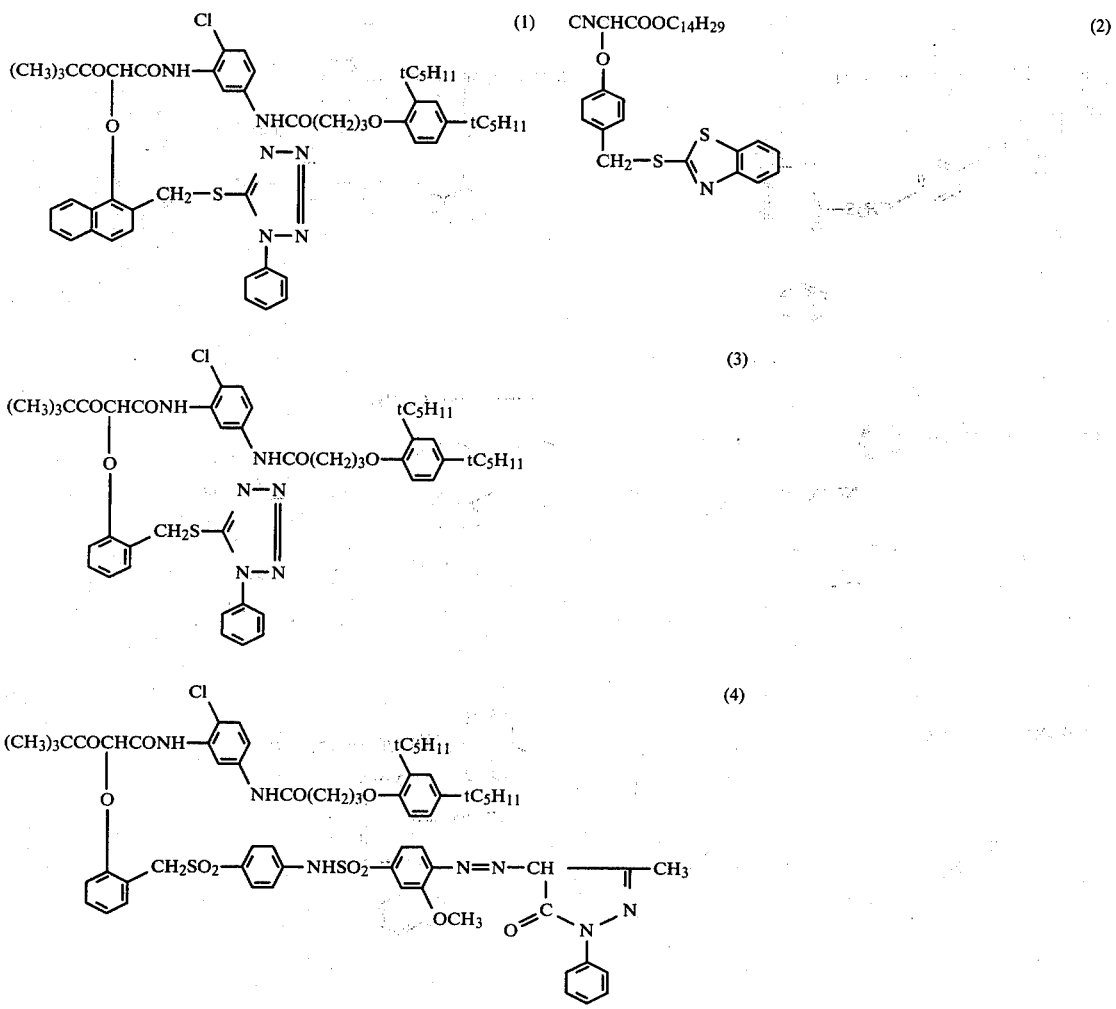

-continued
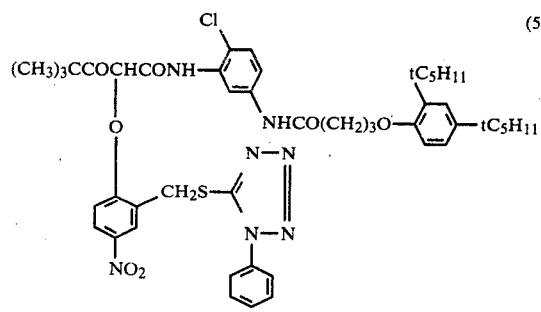 (5)
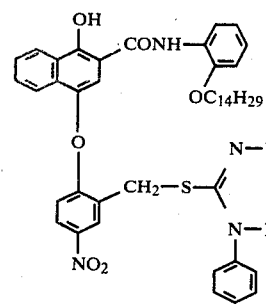 (6)
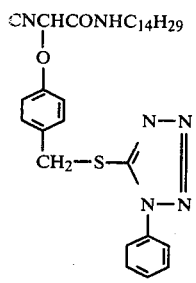 (7)
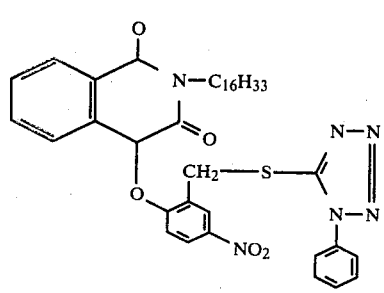 (8)
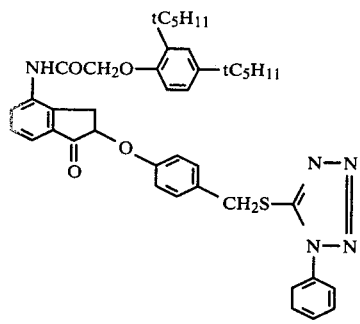 (9)
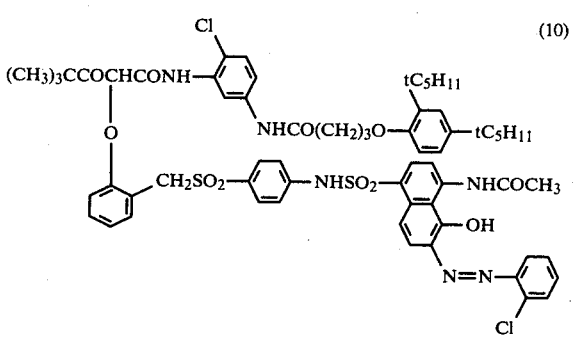 (10)
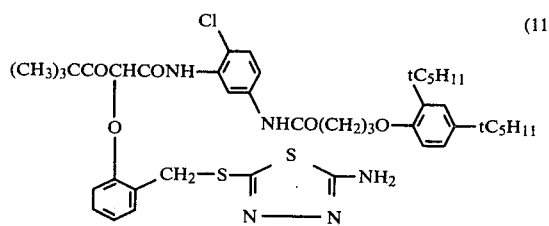 (11)
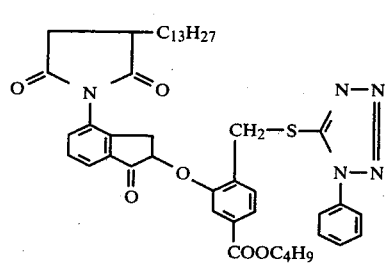 (12)
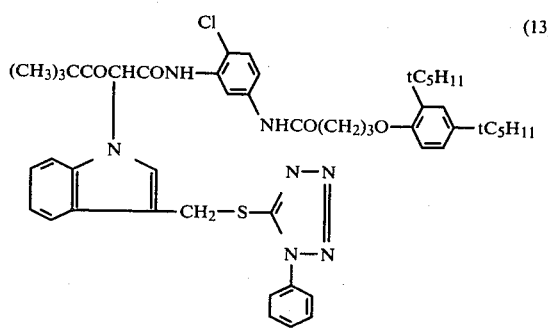 (13)
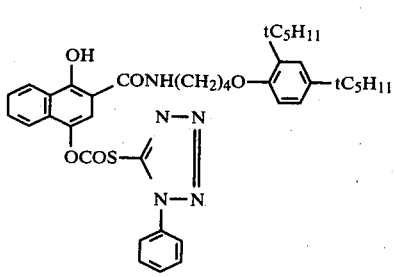 (14)

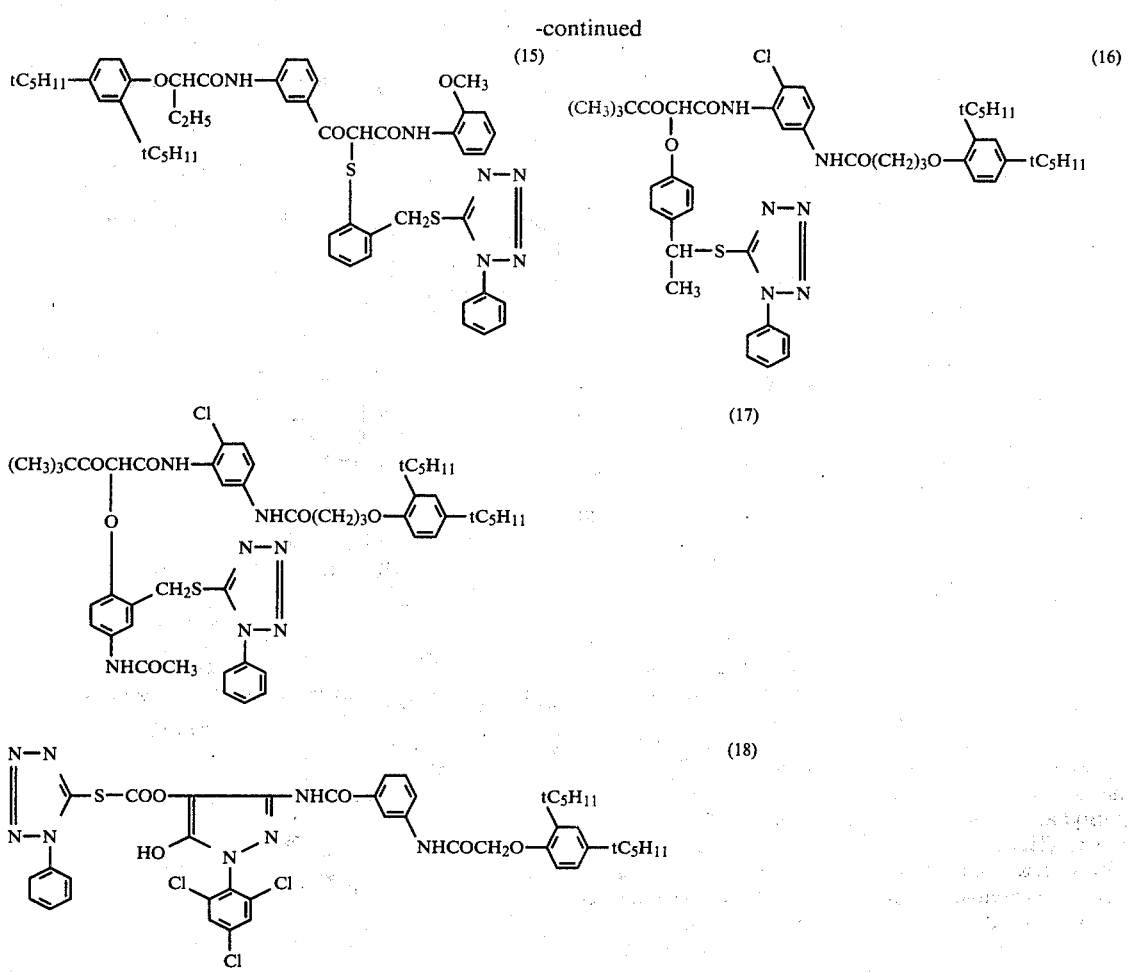

As seen from the above illustrative compounds, the compound of the present invention is characterized in that the component A in the general formula (1) with a timing group bound to the coupling site thereof need not always be a coupler and further there is a large degree of freedom in the selection of the photographically useful group. In addition, being unaffected under the presence of hydroxyl ion in the developer even at the time of cleavage reaction, the compound is convenient in use while it can release the photographically useful group in timing to achieve a higher photographic effect.

The compound of the present invention is synthesized acording to such a conventional way as those synthesizing DIR compounds or DIR couplers.

To illustrate the synthesis of compounds of the present invention, examples are given below:

EXAMPLE OF SYNTHESIS 1–COMPOUND (3)

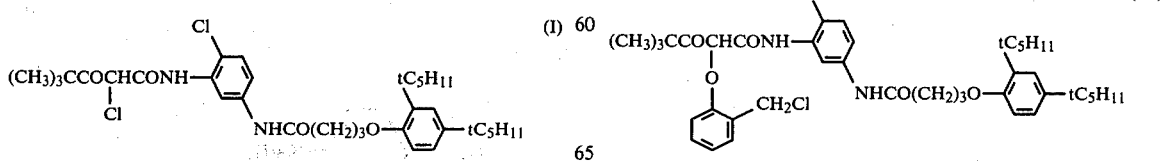

-continued

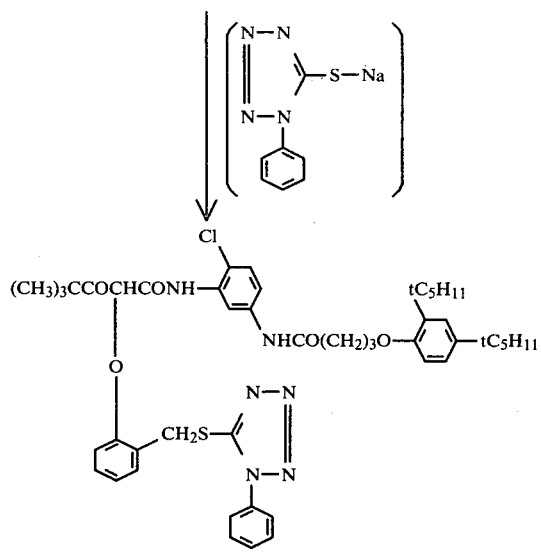

12 g of the potassium salt of o-hydroxybenzyl alcohol and 30 g of the compound (I) were dissolved in 500 ml of acetonitrile and boiled for 1.5 hr under agitation. Actonitrile was evaporated from the solution to leave residues, from which the extraction was made with use of ethyl acetate. The ethyl acetate extract was subjected to the silica gel chromatography using the benzene/ethyl acetate mixed solvent for elution. 22 g of the compound (III) was thus produced. 11 g of this compound was dissolved in 100 ml of chloroform and 3.3 g of phosphorus pentachloride was added to the resultant solution at its cold state. The solution was agitated 1 hr as it was. The reaction solution was fully washed with water and chloroform was evaporated from the solution. The residues were subjected to the silica gel chromatography using the benzene/ethyl acetate mixed solvent for elution. 7.3 g of the compound (III) was thus produced. This compound was identified using the nuclear magnetic resonance spectroscopy. Namely, 5 g of the product compound (III) was dissolved in 100 ml of acetone. After the addition of 1.8 g of the sodium salt of 1-phenyl-5-mercaptotetrazole, the solution was boiled 30 min under agitation. Acetone was then evaporated from the solution to leave residues, from which the extraction was made with use of ethyl acetate. The extract was washed with 3% aqueous sodium carbonate and then with water and ethyl acetate was evaporated from the extract to leave 5.8 g of the target substance in the caramelized state, which was identified by the nuclear magnetic resonance spectroscopy.

EXAMPLE OF SYNTHESIS 2-COMPOUND (14)

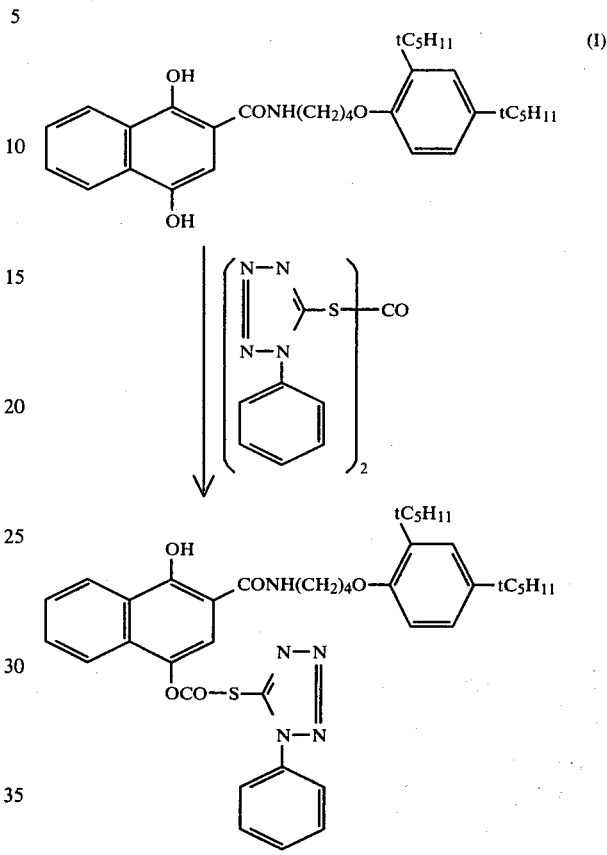

9.8 g of the compound (I) was dissolved in 200 ml of ethyl acetate and then 7.7 g of S,S'-carbonyl-di-1-phenyl-5-mercaptotetrazole (prepared by bubbling phosgene into a benzene solution of 1-phenyl-5-mercaptotetrazole) was added to the resultant solution. The reaction mixture was agitated 2 hr at room temperature and then the reaction solvent was evaporated under a reduced pressure. The residues that were left were passed through a silica gel column with use of a benzene/hexane mixed solvent for the chromatographic separation of the product. Fractions that contained the pure product were joined and the solvent was evaporated under a reduced pressure to leave 8.9 g of the target substance in the caramelized state, which was identified by the nuclear magnetic resonance spectroscopy.

EXAMPLE OF SYNTHESIS 3-COMPOUND (4)

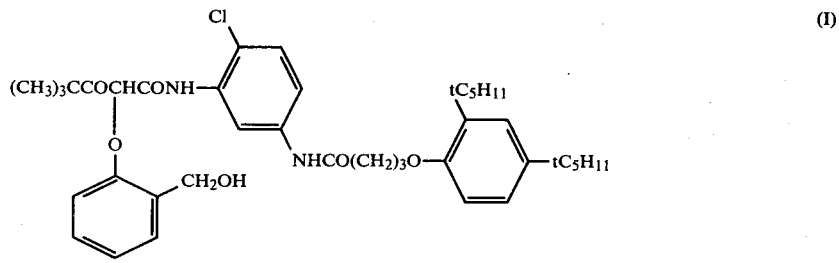

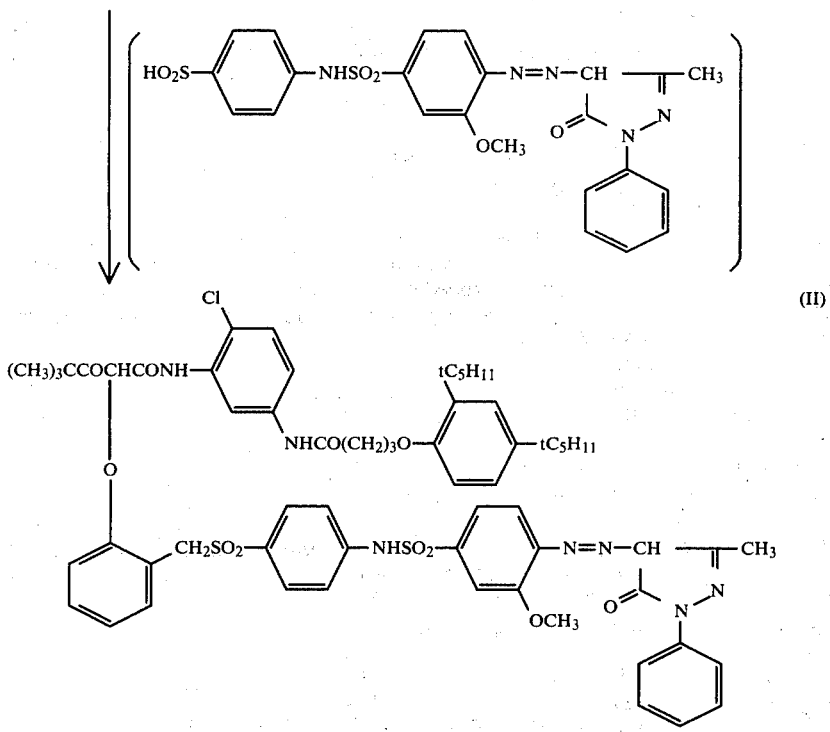

8.15 g of 4-(1-phenyl-3-methyl-5-pyrazolon-4-ylazo)-3-methoxybenzenesulfonyl chloride, 3.2 g of 4-aminobenzenesulfinic acid and 2.4 g of dimethylaniline were put into 15 ml of dimethylformamide and the mixture was agitated 3 hr at 20° C. The reaction solution was then poured into 400 ml of 2 N hydrochloric acid. A dye that was produced was salted out as sulfinic acid. 8.0 g of the compound (II) was thus obtained.

6.9 g of the compound (I) was dissolved in 200 ml of acetic acid while 5.3 g of the compound (II) was dissolved together with 1.1 g of sodium acetate in 50 ml of 80% ethanol. Both solutions were mixed with each other and after the addition of 0.4 ml of concentrated sulfuric acid the resultant solution was boiled 5 hr under agitation. The reaction solution was poured into water for the extraction with ethyl acetate. The ethyl acetate extract was washed with 5% aqueous sodium acetate and then with water. After the evaporation of the solvent, the residues were subjected to the silica gel chromatography. The separated compound was recrystallized from methanol. 1.5 g of the compound (4) was thus obtained.

Other compounds given above as the illustrative examples can be synthesized correspondingly to one of the above three examples of synthesis.

The photographic material containing a compound of the present invention can be processed for the color development, bleaching, and fixing, or according to the processing steps that are applied to the conventional color reversal material. Further, it can be processed for the image intensification using oxidizing agents, for example, complex compounds of transition metals such as cobalt hexamine and peroxides such as hydrogen peroxide as disclosed in U.S. Pat. Nos. 3,674,490, 3,822,129, 3,834,907, 3,841,873, 3,847,619, 3,862,842, 3,902,905, and 3,923,511.

The photographic material to be loaded with a compound of the present invention may be a single or multiple silver halide emulsion layer or layers formed on a base.

The multi-layer color photographic material is usually composed of at least a red sensitive emulsion layer, green sensitive emulsion layer and blue sensitive emulsion layer formed on a base in any proper order to satisfy the particular requirement. Usually, the red, green and blue sensitive emulsion layers are loaded with a cyan, magenta and yellow couplers, respectively, though different combinations may be used as adequate.

Further, the photographic material of the present invention may be composed of a single layer formed on a base and loaded with a black and white image forming coupler for the black and white photography.

A compound of the present invention may be loaded into a sensitive silver halide emulsion layer of these photographic materials or a layer adjacent thereto and one or simultaneously two or more of these structural layers or unit layers may be used for the above loading.

To load the photographic material, the compound of the present invention may be used in a quantity of about 0.01 to 3 mol per mol of silver halide.

The compound of the present invention may be loaded into the photographic material by various methods, typical examples of which are as follows:

(a) The compound of the present invention is dissolved in an organic solvent of high boiling point hardly miscible with water and the resultant solution is emulsified into an aqueous medium for dispersion to add to the photographic emulsion.

(b) The compound of the present invention is dissolved in an organic solvent of low boiling point less miscible with water and the resultant solution is emulsified into an aqueous medium for dispersion to add to the photographic emulsion. The solvent used is removed during the manufacturing process of the photographic material.

(c) The compound of the present invention is dissolved in an organic solvent readily miscible with water and the resultant solution is added to the photographic emulsion, when the compound is dispersed in the form of colloidal particles.

The above three kinds of solvents may be mixed for use and/or a dispersing agent may be added depending on the solubility of the compound of the present invention.

In case the timing group with a photographically useful group attached thereto or the photographically useful group itself is diffusive, a scavenger layer or layers may be interposed at a proper position or positions between the structural layers of the photographic material so as to control the structural layers or unit layers to be affected by the above photographically useful group.

The silver halide used in the photographic material of the present invention may be prepared by a method of conventional practice, being silver chloride, silver bromide, silver chlorobromide, silver iodobromide or silver chloroiodobromide in composition. A silver halide emulsion may be prepared from the above silver halide by an ordinary method and further it may be chemically sensitized.

For the above chemical sensitization, a known chemical sensitizer may be used. Further, this emulsion may be loaded with additives of ordinary use, such as the sensitizing dye, antifoggant, hardening agent, plasticizer and surfactant.

As for the silver halide emulsions and additives, a more detailed description is given in "Research Disclosure", December, 1971, p. 9232.

The compound of the present invention can be added to the photographic material for various objects and in various dispositions according to the action and property of individual photographically useful residues. It may be mixed with various couplers and other additives, as necessary. Further, in case the photographically useful group to be released from the compound of the present invention is a development inhibitor, the compound may be used, for example, with such photographic materials as disclosed in U.S. Pat. Nos. 3,227,554, 3,620,747 and 3,703,375.

As described in detail in the above, in the compound of the present invention, a photographically useful group is bound through a timing group to a compound that can undergo a coupling reaction, so the above photographically useful residue can be released indirectly. Therefore, through the use of this compound, the action and effect of the photographically useful residue can be controlled both in timing and in spatial relation. Thus, compared to the interimage effects given by the development inhibitor releasing couplers or DIR couplers as disclosed in U.S. Pat. No. 3,227,554 and the development inhibitor releasing compounds or DIR compounds as disclosed in U.S. Pat. No. 3,958,993, more excellent interimage effects may be expected from the compounds of the present invention.

To further illustrate the present invention, and not by way of limitation, the following examples are given.

EXAMPLE 1

15 g of a magenta coupler 1-(2,4,6-trichlorophenyl)-3-[3-(2,4-di-t-amylphenoxyacetamido)benzamido]-5-pyrazolone was dissolved in a mixture of 30 ml of ethyl acetate and 15 ml of dibutyl phthalate. The resultant solution was added to a mixture of 20 ml of 10% aqueous Alkanol B (supplier: Du Pont) and 200 ml of 5% aqueous gelatin and the solution was emulsified for dispersion in a colloid mill. Thereafter, this dispersed solution was added to 1 kg of green sensitive silver iodobromide emulsion containing 3.0 mol% of silver iodobromide. After dispersion, the emulsion was applied to a triacetate base and dried to give a control Sample (1).

In addition to the above control sample (1), control Samples (2), (3) and (4) were prepared by repeating the above procedure but adding the following three DIR couplers, respectively, in quantities as specified in Table 1.

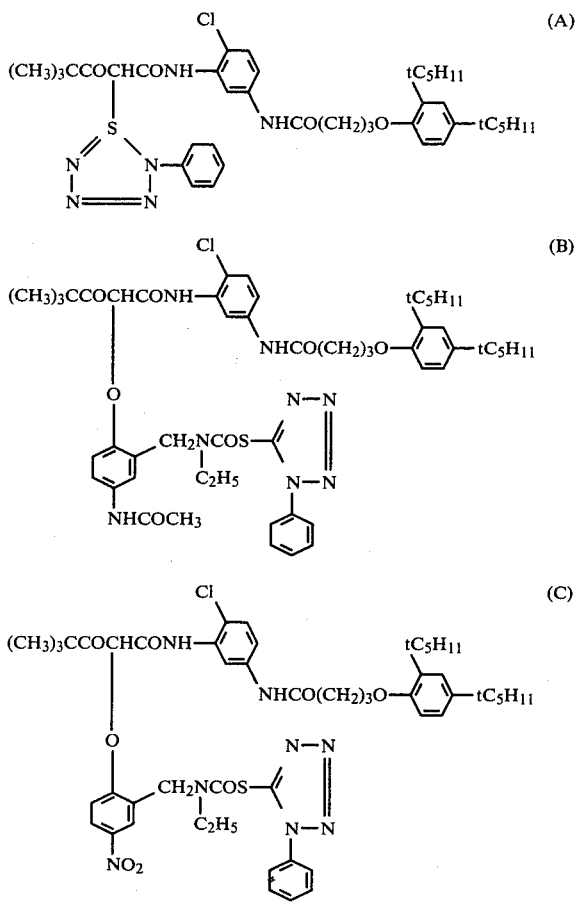

(B) and (C) are those disclosed in GB 2010818A.

Further, Samples (5) and (6) were prepared by repeating the procedure for the preparation of the Sample (1) but adding the compounds (3) and (5) as described for the compound of the present invention in quantities as specified in Table 1.

TABLE 1

| Sample No. | Added compound | Quantity in g | Quantity in mols |
|---|---|---|---|
| 1 | — | — | — |
| 2 | DIR coupler (A) | 0.98 | $1.30 \times 10^{-3}$ |
| 3 | DIR coupler (B) | 1.29 | $1.30 \times 10^{-3}$ |
| 4 | DIR coupler (C) | 1.27 | $1.30 \times 10^{-3}$ |
| 5 | Compound (3) | 1.10 | $1.30 \times 10^{-3}$ |

TABLE 1-continued

| Sample No. | Added compound | Quantity in g | Quantity in mols |
|---|---|---|---|
| 6 | Compound (5) | 1.18 | $1.30 \times 10^{-3}$ |

The above six samples were subjected to a wedge exposure, processed 3 min at 38° C. in color developing bath of the following formulation, bleached, fixed and then washed with water.

| Formulation of the color developing bath: | |
|---|---|
| 4-amino-3-methyl-N—ethyl-N—(β-hydroxyethyl)-aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g |
| Water was added to make up to a liter of solution and its pH was adjusted to 10.0 using potassium hydroxide. | |

The results thus obtained are shown in the following Table 2.

TABLE 2

| Sample No. | Added compound | Relative sensitivity | Gamma |
|---|---|---|---|
| 1 | — | 100 | 1.20 |
| 2 | DIR coupler (A) | 74 | 0.76 |
| 3 | DIR coupler (B) | 64 | 0.94 |
| 4 | DIR coupler (C) | 44 | 0.45 |
| 5 | Compound (3) | 81 | 1.03 |
| 6 | Compound (5) | 62 | 0.53 |

As seen from the Table 2, the release of the development inhibitor lowered the density less and more in the Samples (5) and (6), respectively, of the present invention than in the control Sample (2). This indicates that the release of the development inhibitor may be controlled in its timing and rate just by modification of the timing group. Further, a comparison of the control Samples (3) and (4) to the Samples (5) and (6) of the present invention in sensitivity shows that there was a release of the development inhibitor due to the decomposition caused by hydroxyl group other than coupling reaction in these two control samples.

EXAMPLE 2

Samples (7), (8) and (9) were prepared as in Example 1 but for the use of 10.6 g of cyan coupler -hydroxy-N-[4-(2,4-di-t-amylphenoxy)butyl]-2-naphthamide, instead of the magenta coupler, and the following DIR coupler and compound (14) of the present invention added according to Table 3. These three samples were exposed and processed for development as in Example 1.

DIR coupler (D):

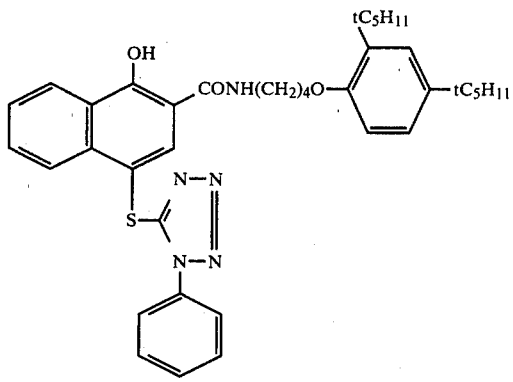

The results thus obtained are shown in Table 3.

TABLE 3

| Sample No. | Added compound | Added qty in mols | Relative sensitivity | Gamma |
|---|---|---|---|---|
| 7 | — | — | 100 | 1.15 |
| 8 | DIR coupler (D) | $1.32 \times 10^{-3}$ | 72 | 0.92 |
| 9 | Compound (14) | $1.32 \times 10^{-3}$ | 63 | 0.67 |

As seen from Table 3, the release of the development inhibitor was more effective, lowering the density more in the Sample (9) of the present invention than in the Sample (8) that was based on the conventional direct coupling type DIR coupler.

EXAMPLE 3

Samples were basically prepared by coating a triacetate base multiply with the following layers in the order of description:

(1) Red sensitive silver iodobromide emulsion layer containing 1.80 g of yellow coupler 2-(2,2-dimethylpropionyl)-2-(1-benzyl-2-phenyl-3,5-dioxo-1,2,4-triazolidin-4-yl)2'-chloro-5'-(α-dodecyloxycarbonyl-ethoxycarbonyl)acetanilide, 2.4 g of gelatin and 1.6 g of silver halide per square meter of base.

(2) Intermediate gelatin layer containing 0.5 g of gelatin and 0.1 g of 2,5-dioctylhydroquinone per square meter of base.

(3) Green sensitive silver iodobromide emulsion layer containing 0.47 g of cyan coupler 1-hydroxy-N-[4-(2,4-di-t-amylphenoxy)butyl]-2-naphthamide, 2.4 g of gelatin and 1.6 g of silver halide per square meter of base. And (4) Protective coating composed of 0.8 g of gelatin per square meter of base.

Among the structural layers of the above multi-layer photosensitive material, the third layer containing a cyan coupler was loaded with a DIR coupler and DIR compound, as represented by the following structural formulas, and compounds (6), (8) and (12) in quantities as specified in Table 4 to prepare Samples (10), (11), (12), (13) and (14), respectively.

DIR coupler (E):

-continued

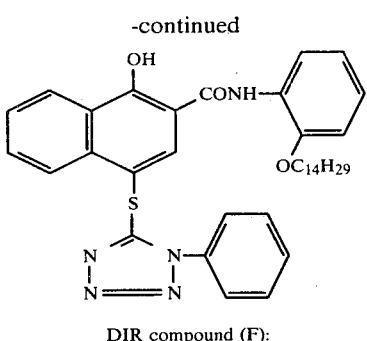

DIR compound (F):

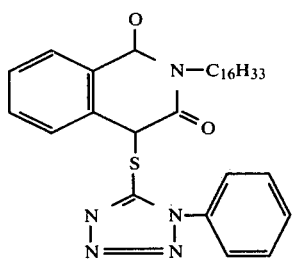

TABLE 4

| Sample No. | Added compound | Quantity in g/m² | Quantity in mols/m² |
|---|---|---|---|
| 10 | DIR coupler (E) | 0.098 | $1.5 \times 10^{-4}$ |
| 11 | DIR compound (F) | 0.084 | $1.5 \times 10^{-4}$ |
| 12 | Compound (6) | 0.118 | $1.5 \times 10^{-4}$ |
| 13 | Compound (8) | 0.107 | $1.5 \times 10^{-4}$ |
| 14 | Compound (12) | 0.129 | $1.5 \times 10^{-4}$ |

Individual samples were prepared in duplicate for an exposure to white light on the one hand and for a wedge exposure on the other hand. Exposed samples were processed 2 min at 38° C. in a color developing bath of the following formulation, bleached, fixed and washed with water.

| Formulation of the color developing bath: | |
|---|---|
| 4-amino-3-methyl-N—ethyl-N—β-hydroxylethylaniline sulfate | 3.55 g |
| Potassium sulfite | 2.0 g |
| Anhydrous potassium carbonate | 30.0 g |
| Potassium bromide | 1.25 g |
| Potassium iodide | 0.0006 g |

Water was added to make up to 1 liter of solution. pH was 11.0.

For individual samples, gammas were estimated from the characteristic curve for the yellow dye produced by the color development. The ratio of the gamma estimated for the exposure to red light ($\gamma R$) to the gamma for the exposure to white light ($\gamma W$) was calculated with individual samples. The results are given in Table 5.

TABLE 5

| Sample No. | Added compound | $\gamma R/\gamma W$ |
|---|---|---|
| 10 | DIR coupler (E) | 1.12 |
| 11 | DIR compound (F) | 1.15 |
| 12 | Compound (6) | 1.69 |
| 13 | Compound (8) | 1.51 |
| 14 | Compound (12) | 1.75 |

As seen from the above table, all the Samples (12), (13) and (14) of the present invention showed larger estimates for $\gamma R/\gamma W$ than the control Samples (10) and (11). This meant that the samples of the present invention contained the development inhibitor in larger quantities than the control samples. In other words, it was clearly indicated that the use of a compound of the present invention gives larger inter-image effects than the use of a DIR coupler or compound of the conventional use.

What is claimed is:

1. A photographic material comprising a light sensitive silver halide emulsion layer provided on a support, said material containing a compound represented by the formula:

A-TIME-PUG, wherein A is a coupler group capable of a coupling reaction with an oxidized color developing agent, PUG is a photographically useful group, and TIME is a timing group joining said coupler and said photographically useful group and further wherein said timing group is cleavable from said coupler group on reaction of said coupler group with said oxidized color developing agent and further wherein the resulting cleaved timing and photographically useful group entity-TIME-PUG is able to undergo electron transfer along a conjugated system therein to cleave the PUG after the group-TIME-PUG is cleaved from said coupler group A and further wherein one end of TIME is connected with PUG through a methylene group contained in TIME and substituted by R1 and R2, wherein R1 and R2 are individually a hydrogen atom, an alkyl group or an aryl group and wherein the other end of TIME is connected to A at the coupling site of A through an O, S or N atom contained in TIME.

2. A photographic material according to claim 1 wherein the TIME is represented by the following formula:

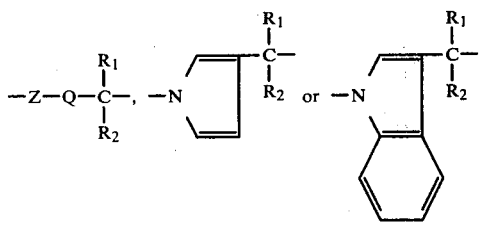

wherein the left hand side is attached to the coupler group; Z is O, S or

$R_1$, $R_2$ and $R_3$ are individually hydrogen, alkyl or aryl groups; and Q is a 1,2- or 1,4-phenylene or naphthylene group.

3. A photographic material according to claim 1 wherein the PUG is development inhibitor or accelerator, bleach inhibitor or accelerator, developing agent, fixing agent, hardening agent, tanning agent, toning agent, fogging agent, antifogging agent, chemical or optical sensitizer or desensitizer, photographic dye, or coupler.

4. A photographic material according to claim 3 wherein the PUG is development inhibitor, bleach inhibitor or photographic dye.

5. A photographic material according to claim 3 wherein the PUG is development inhibitor.

6. A photographic material according to claim 5 wherein the development inhibitor is mercaptotetrazole, selenotetrazole, mercaptobenzothiazole, selenobenzothiazole, mercaptobenzooxazole, mercaptobenzimidazole, selenobenzimidazole, benzodiazole or benzotriazole compound.

7. A photographic material according to claim 6 wherein the development inhibitor is mercaptotetrazole, mercaptobenzothiazole or mercaptobenzimidazole compound.

8. A photographic material according to claim 7 wherein the development inhibitor is mercaptobenzotetrazole compound.

9. A photographic material according to claim 1 wherein the coupler group is a dye forming photographic coupler from which hydrogen atom attached to coupling position is released.

* * * * *